July 28, 1953
P. ECKE
Plant Pat. 1,207
POINSETTIA PLANT
Filed May 13, 1952
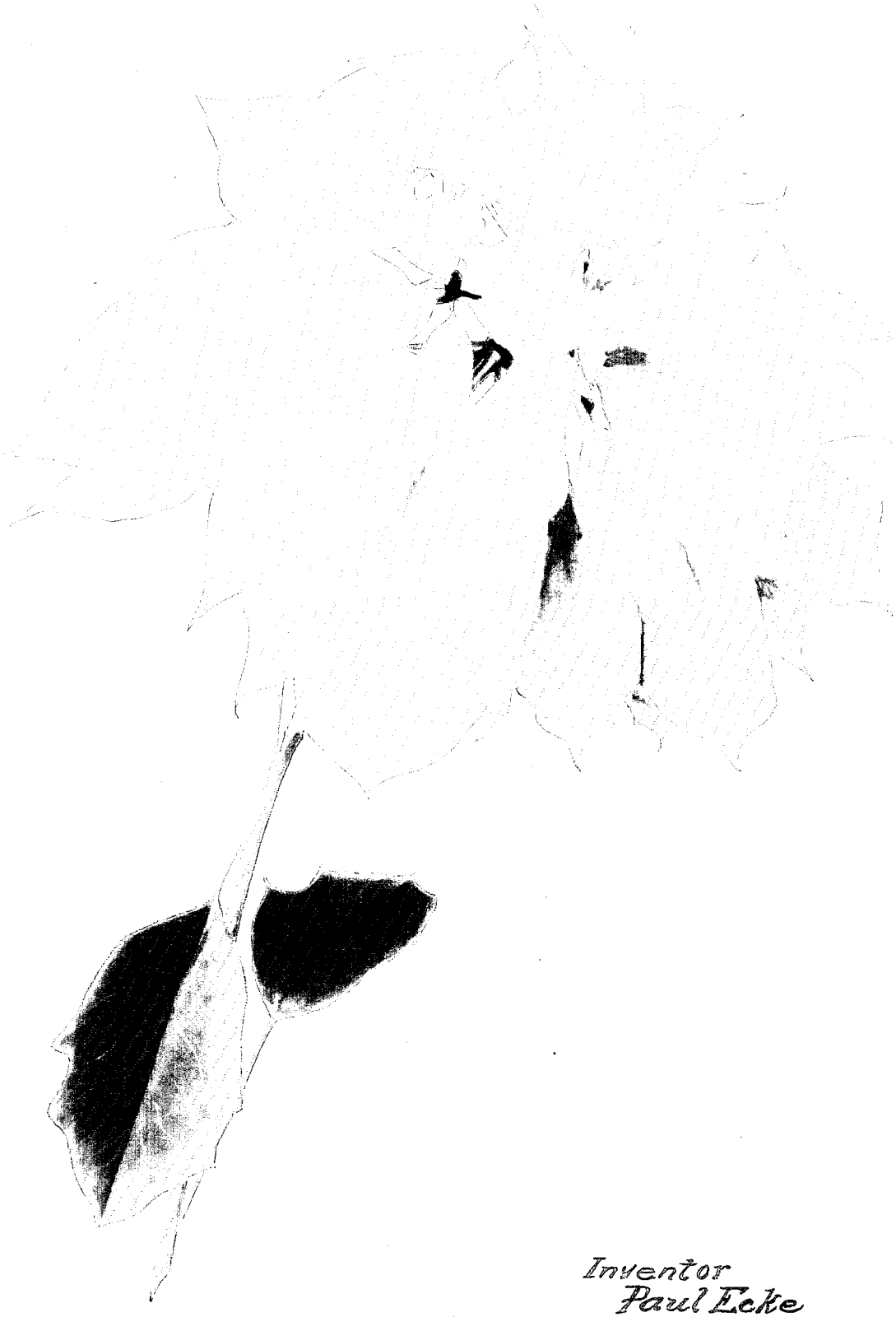
Inventor
Paul Ecke
by Wm. J. Graham
Attorney Patented July 28, 1953

Plant Pat. 1,207

UNITED STATES PATENT OFFICE 1,207

POINSETTIA PLANT

Paul Ecke, Encinitas, Calif.

Application May 13, 1952, Serial No. 287,454

1 Claim. (Cl. 47—60)

The present invention or discovery relates to a new and distinct variety of poinsettia plant (*Euphorbia pulcherrima*), originating as a sport.

Broadly, this new variety of poinsettia plant is distinguishable from the parent plant as well as from other known varieties, mainly in the shape, color, profuseness and character of arrangement of the bracts and foliage leaves. More specifically, it is also distinguishable from other known varieties by a secondary growth of clusters of relatively small bracts at an open center of larger bracts, the latter being profuse in overlying layers, the individual bracts being relatively long, wide, and ovate-acuminate, a majority of which are mounted on radiating comparatively long petioles so that the bract involucre is open at its center providing space for the clusters of smaller bracts which grow upstandingly from the center beyond the general plane of the upper face of the larger bracts and provide an appearance of unusual thickness to the body of the bloom.

The accompanying illustration, forming a part of this application, graphically shows in color, contour and detail this new variety in its full maturity or optimum, the illustration being a face view of the subject, shown in its normal condition, with its characteristics which differentiate this new variety, the darker colored bracts at the left side of the drawing being to indicate shadow and not a variation of color.

The colors referred to herein correspond approximately with those shown in "Horticultural Color Chart" issued by the British Color Council in collaboration with the Horticultural Society, and identified by the color name and plate of said color standard by recapitulation in tabular form herein.

The following is a detailed description of this new variety.

*Parentage*

This new variety was originated and discovered by me in a cultivated area of a glasshouse or greenhouse at my experimental and growing gardens at Encinitas, San Diego County, California, and originated as a cultivated sport of poinsettia plant of the variety commonly known as the Albert Ecke poinsettia plant, not patented, but also originated by me, and known in the trade by that name for many years.

The new variety has been asexually reproduced in my greenhouse or glasshouse by cuttings, and it has remained true to type and to the herein described characteristics, through the propagation of several thousands plants over a period of more than three (3) years and has shown its qualities and characteristics to be permanently fixed.

*Structure*

The peduncles which branch from the main trunk are spinach green and are long, stiff and very strong. They are comparatively small in cross section, unusually so, compared to the large and relatively compact heavy cluster of bracts. Their average length is four feet, at the upper free end of which grows an involucre of bracts.

*Foliage leaves*

The foliage leaves are arranged around the peduncle and are usually in groups of three, the petioles of which radiate from the peduncle in longitudinally widely spaced relation.

The foliage leaves are of a modified oak-leaf type, generally ovate and moderately scalloped at the outer end portion, and have fishbone venation. The color of the foliage leaves is a shade of spinach green, and the petioles thereof are blood red.

*Bracts*

There are two types of bracts of substantially uniform color and slightly sub-coriaceous.

Firstly, there is a profusion of relatively large bracts providing an involucre radiating outwardly on long petioles from the end of the peduncle, the profusion of large bracts causing them to overlie relatively in the nature of superposed layers and forming an annular wreath substantially open at its center.

The large bracts, in planar contour, are elongated and prolately ovate-accuminate; they are numerically greater in number of individual bracts than known varieties of poinsettia, and the predominating majority of the individual larger bracts are of greater axial length and greater transverse width and greater individual planar area than known varieties providing a wide diameter to the involucre ranging up to six or seven inches.

Secondly, there are small bracts which grow, at the end of the peduncle in the open center of the wreath of larger bracts, where, in other varieties of poinsettia plants, there are flowers. The small bracts are produced usually in clusters of from one to four small bracts at the end of petioles which stand up in the open center of the wreath of larger bracts above the general plane of the larger bracts, and provide a richness and thickness of body having an appearance of thickness intermediately between the headed ball type of my Plant Patent No. 1,052 of December 11, 1951, and the single layer of individual bracts disclosed in my Plant Patent No. 1,068 of January 29, 1952. The small bracts are sometimes regular and some irregular in characteristics of size and shape; sometimes more or less sinuously contorted or even grotesque.

At the optimum of their maturity both types of the bracts and their petioles are blood red in color, and maintain a uniformity of color in a wider differential range of temperature than known varieties of poinsettia plants.

The season for optimum development of the bracts is from mid-November through the following month of February, and the bract involucre has an unusual persistence of months, a period of as much as three months not being unique or extraordinary.

*Inflorescence*

There are no flowers and no reproductive organs such as seed pod, cyathium, or ovules.

*Propagation*

In asexually reproducing this new variety I have found it satisfactory and efficient to cut pieces of stalk of soft wood substantially six inches long in the months of June, July and August, and embed one end of the cutting in beds of sand in my glasshouse. After three to four weeks the cuttings are well rooted and may be transferred to individual pots. The plant will mature to optimum and produce its bracts from November to December, retaining bracts and foliage for substantially ten to twelve weeks, after which the plant will remain dormant for substantially three months.

*Dimensions*

The total height of the plant at maturity, including main trunk and peduncles, is approximately seven feet, and the greatest lateral dimension is approximately four feet.

*Habits of growth*

This new variety has vigorous growth, but grows close-jointed and does not stretch as is the case with some other varieties and, therefore, more desirable for pot-plant purposes. It is easily cultivated, if properly handled, and persistent and perennial in growth. Foliage and bracts occur annually maturing in Southern California from mid-November to the following February, the optimum elsewhere being modified by climate and growing conditions.

*Variations*

Different plants of this new variety have an unusual similarity of adherence to characteristics and type as herein described; however, in comparison with the same growth in various localities, in different soil, and at various times of the year, in different temperatures or in different greenhouses or in the open, and even by different persons, there may be variations of minor detail.

*Color tabulations*

The color designations according to the color plates of said "Horticultural Color Chart" are recapitulated in tabular form as follows:

| Element | Color | Sheet | Plate |
|---|---|---|---|
| Peduncles | Spinach Green | 187 | o960/3 |
| Foliage Leaves | do | 187 | o960/2 |
| Petioles of Foliage Leaves | Blood Red | 166 | 820/2 |
| Bracts | do | 166 | 820/3 |
| Petioles of Bracts | do | 166 | 820/3 |

Having described and illustrated my new variety of poinsettia plant, I claim:

A new and distinct variety of poinsettia plant substantially as illustrated and described, characterized by an apparent absence of flowers and by a first group of bracts comprising a profusion of relatively large bracts radiating on relatively long petioles from the peduncle, the individual large bracts being ovate-accuminate and comparatively wide throughout the major portion of their axial length whereby next adjacent bracts overlaps at edge portions providing an involucre wreath open at its central portion, and further characterized by a second group of relatively smaller bracts which grow from the peduncle on relatively long upstanding petioles at said open center of the involucre of the larger bracts, the smaller bracts being irregular in shape and size and generally having more than one bract to each petiole, said bracts of both groups being of a blood red color.

PAUL ECKE.

No references cited.